United States Patent [19]

Gajo

[11] Patent Number: 5,458,138
[45] Date of Patent: Oct. 17, 1995

[54] NASOPHARYNGEAL FLUID SUCTION DEVICE

[76] Inventor: Alden H. Gajo, 743 Michigan La., Elk Grove Village, Ill. 60007

[21] Appl. No.: 136,601

[22] Filed: Oct. 14, 1993

Related U.S. Application Data

[63] Continuation of Ser. No. 526,983, May 23, 1990, abandoned.

[51] Int. Cl.⁶ ..................................................... A62B 9/02
[52] U.S. Cl. ............................. 128/205.24; 128/205.12; 604/319
[58] Field of Search ................... 128/10, 200.26, 128/207.14, 207.15, 207.16, 205.12, 205.24; 604/19, 27, 35, 76, 316, 317, 319, 221; 251/5, 9

[56] References Cited

U.S. PATENT DOCUMENTS

| | | | |
|---|---|---|---|
| 1,468,887 | 9/1923 | Sterrick | 251/342 |
| 2,518,165 | 8/1950 | Millard | 251/342 |
| 2,692,751 | 10/1954 | Felver | 251/342 |
| 2,700,973 | 2/1955 | Ju | 604/317 |
| 2,706,101 | 4/1955 | Cantor | 251/342 |
| 3,750,692 | 8/1973 | Tibbs | 604/321 |
| 3,757,783 | 9/1973 | Alley | 604/321 |
| 3,896,810 | 7/1975 | Akiyama | 604/316 |
| 4,142,645 | 3/1979 | Walton | 251/342 |
| 4,267,835 | 5/1981 | Barger et al. | 251/342 |
| 4,384,580 | 5/1983 | Leviton | 604/319 |
| 4,397,643 | 8/1983 | Rygiel | 604/317 |
| 4,402,687 | 9/1983 | Denty et al. | 604/319 |
| 4,455,140 | 6/1984 | Joslin | 604/317 |
| 4,650,477 | 3/1987 | Johnson | 604/321 |
| 4,699,138 | 10/1987 | Behrstock | 128/207.16 |
| 4,729,765 | 3/1988 | Eckels et al. | 128/207.16 |
| 4,730,635 | 3/1988 | Linden | 251/342 |
| 4,735,606 | 4/1988 | Davidson | 604/321 |
| 4,787,894 | 11/1988 | Turnbull | 128/207.14 |
| 4,791,914 | 12/1988 | May | 128/760 |
| 4,813,931 | 3/1989 | Hauze | 128/760 |
| 4,850,350 | 7/1989 | Jackson | 128/207.16 |
| 4,867,153 | 9/1989 | Lorenzen et al. | 128/205.12 |
| 4,913,401 | 4/1990 | Handke | 251/342 |
| 4,947,841 | 8/1990 | Ng | 128/207.14 |
| 5,000,175 | 3/1991 | Pue | 128/207.16 |
| 5,022,422 | 6/1991 | di Palma | 251/342 |
| 5,139,018 | 8/1992 | Brodsky et al. | 128/207.16 |

FOREIGN PATENT DOCUMENTS

| | | | |
|---|---|---|---|
| 0000399 | 1/1979 | European Pat. Off. | 604/316 |
| 2103187 | 8/1971 | Germany | 604/316 |

*Primary Examiner*—Edgar S. Burr
*Assistant Examiner*—Aaron J. Lewis
*Attorney, Agent, or Firm*—Ladas & Parry

[57] ABSTRACT

Nasopharyngeal fluid suction devices are used for clearing liquid secretions from a human's airway. However, the prior art devices have a potential disadvantage in that the operator's mouth may be contaminated by suction liquid, and further that operator-assisted coordination frequently occurs resulting in poor timing, less effective and longer duration suction time. To overcome these disadvantages a body fluid suction device is provided having a catheter for collecting liquid secretions from the nasopharynx coupled to a flexible tubing for transporting the suctioned liquid and gaseous materials. A regulating valve is coupled to the flexible tubing and is responsive to external positive pressure to regulate the suction flow. An extension tubing adapter couples the regulating valve to a source of suction.

1 Claim, 4 Drawing Sheets

NASOPHARYNGEAL FLUID SUCTION DEVICE

This is a continuation of application Ser. No. 07/526,983 filed on May 23, 1990 now abandoned.

BACKGROUND OF THE INVENTION

1. Field of the Invention

This invention relates to nasopharyngeal fluid suction devices specifically for clearing liquid secretions from an infant's airway during delivery in a hospital environment.

2. Description of the Prior Art

Various types of body fluid collection devices with a catheter connectable to a source of suction have been used for collecting liquid secretions from an infant's airway during delivery. For example and most popular prior to awareness of the existence of AIDS (Acquired Immune Deficiency Syndrome) virus is the DeLee suction. In this type of system, a catheter for collecting body fluid is connected in series to a suctioned fluid collection canister further connected to a flexible tubing terminating in a mouthpiece. Suction pressure is provided by the operator's mouth. The obvious disadvantage of this system is the continuity of the circuit that allows suctioned liquid to enter and contaminate operator's mouth at times of canister overflowing or tilting and further allows suctioned gaseous and aerosol materials to enter operator's mouth at all times during use.

Another suction device of prior art is that of a flexible straight catheter with or without suctioned fluid collection canister connectable to a source of external suction pump. In this particular application, an intermittent suction as needed is most effective and desirable. Hence, to enable its operator/s to create an intermittent suction said devices are provided with orificial vent or opening that breaks the continuity of the tube system diverting suction pressure to ambient air when such orificial vent is at uncovered position. Sealing the orificial vent with a finger, usually that of an assistant, allows transmission of undivided suction pressure to catheter end. Intermittent sealing of the vent creates intermittent suction. With two persons operating the suction, operator-assistant incoordination frequently occurs resulting in poor timing, less effective and longer duration of suction time.

Thus, what is needed in the art is a nasopharyngeal suction system which overcomes the above mentioned disadvantages of the prior art. It should provide the operator full control of the suction and eliminates the risk of exposure to biohazardous suctioned materials. Such an invention is described and claimed herein.

SUMMARY OF THE INVENTION

A first aspect of the present invention includes a flexible catheter for collection of liquid secretions from the infant's airway connected in series to a collection canister, flow tubing, flow regulator valve and extension tubing adapter in the order as mentioned. Suctioned fluid is allowed to travel from the infant to canister's chamber through lumen of said catheter. Means is provided for entry of catheter distal end into chamber of the canister without disrupting integrity of canister's vacuum seal. Suctioned fluid entering canister remains on the bottom of the chamber by force of gravity. Flow regulator valve as above mentioned is to be controlled by the operator without an assistant.

In accordance with the principles of the present invention, a nasopharyngeal fluid suction device is created that allows the operator an unassisted, well-coordinated, properly timed and effective intermittent suction and eliminates the risk of operator contamination with suctioned materials.

Furthermore, the present invention provides an economical, disposable device that eliminates the need for cleaning.

These, as well as other objects and advantages of the present invention, will become apparent from the following detailed description and accompanying drawing.

DETAILED DESCRIPTION OF THE PREFERRED EMBODIMENTS

Figure 1:
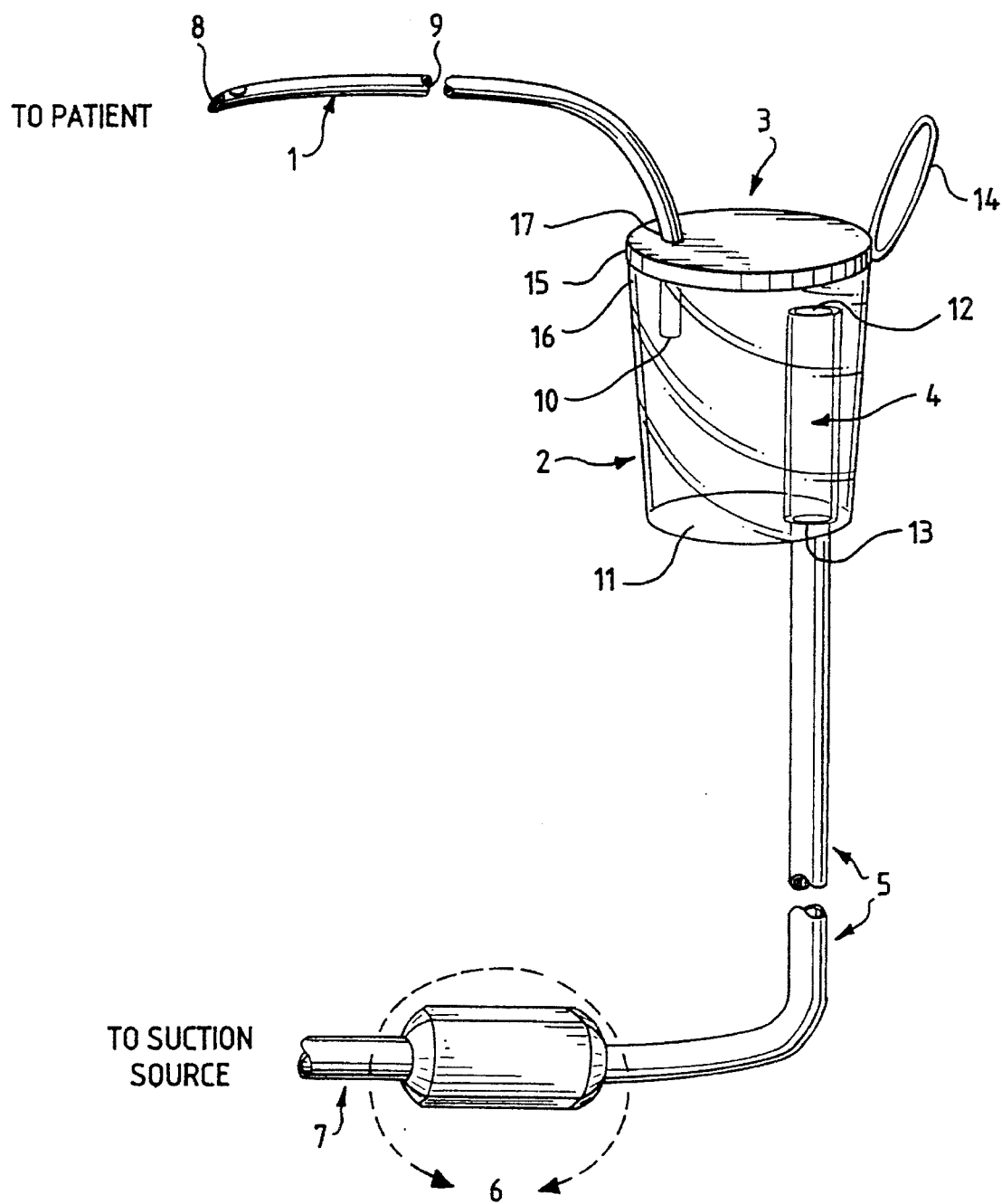
FIG. 1 is a perspective illustration of the nasopharyngeal fluid suction device of the present invention which illustrates a flow regulator valve connected to a suction apparatus.

Referring specifically to FIG. 1 of the accompanying drawing, a nasopharyngeal fluid suction device is shown connected to drain liquid secretions from the infant's nose, mouth and throat indicated at 8. Apparatus is shown including a catheter 1 connected in series to suctioned fluid collection canister 2. Same canister is provided with an air-tight sealing cover lid 3 with a clamp anchor loop 14.

Catheter 1 has main drainage lumen 9 that opens into proximal end 8 to collect liquid secretions from the patient and distal end 10 to deliver collected fluid inside the canister's 2 chamber.

Canister 2 comprises of translucent rigid material cylindrically shaped and allowing view and quantification of suctioned materials. Bottom wall 11 is a molded continuity of the side walls. The canister 2 also includes a replaceable top wall or lid 3 of molded flexible material provided with a collar rim 15 with an internal annular flange to snap receive securely the upper end 16 of the canister 2. Lid 3 is further provided with an aperture 17 serving as point of catheter 1 entry into inside chamber of canister 2.

Flow tube 4 vertically disposed within chamber of canister 2 consists of central lumen with top opening 12 and bottom opening 13. Top opening 12 is close to but not covered by lid 3. Bottom opening 13 leads to outside of canister's 2 chamber connecting to outflow tract flexible tubing 5.

Another aspect of the present invention is a suction pressure flow regulator valve 6 serving to control flow of suction to suction apparatus. Flow regulator valve 6 is connected in series to outflow tract flexible tubing 5 on one end and extension tubing adapter 7 on the other end.

Figure 2:
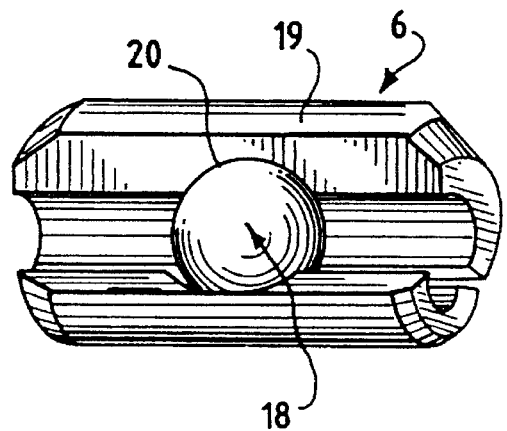
FIG. 2 is a perspective view of flow regulator valve as shown in open condition.

Referring to FIG. 2 is a perspective view of the flow regulator valve 6 of elastomer material 19 shown in open condition. Elastomer material 19 forms complete circumferential wall enclosing a solid ball 18. Points of surface contact 20 between solid ball 18 and elastomer material 19 forms complete circumferential seal allowing no suction pressure transmission beyond flow regulator valve 6 at resting position.

Figure 3:
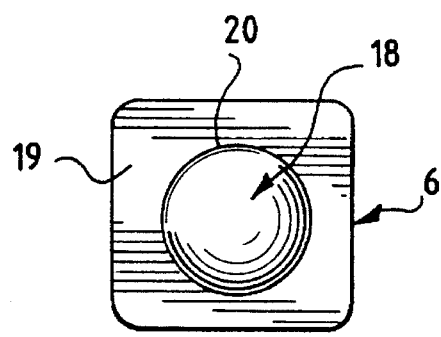
FIG. 3 is an schematic elevational mid-cross section view of flow regulator valve shown at resting or OFF position.

Referring to FIG. 3 is an schematic elevational mid-cross section view of flow regulator valve 6 shown at resting or OFF position. Points of surface contact 20 between elastomer material 19 and solid ball 18 forms complete circumferential seal.

Figure 4:
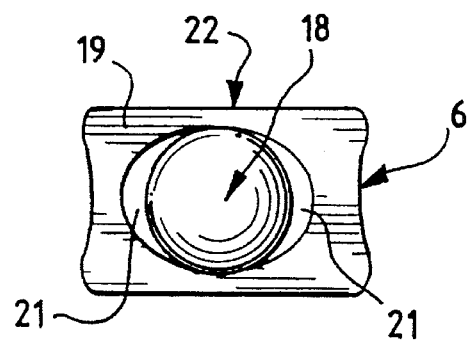
FIG. 4 is an schematic elevational mid-cross section view of flow regulator valve shown at compressed (external positive pressure) or ON position.

Referring to FIG. 4 is an schematic elevational mid-cross section view of flow regulator valve 6 shown at end-compression or ON position. External positive pressure applied 22 on top of flow regulator valve 6 against a hard surface forcing elastomer material 19 to elongate to sides, points of least resistance creating a gap 21 on seal allowing suction pressure transmission beyond flow regulator valve 6.

Figure 5:
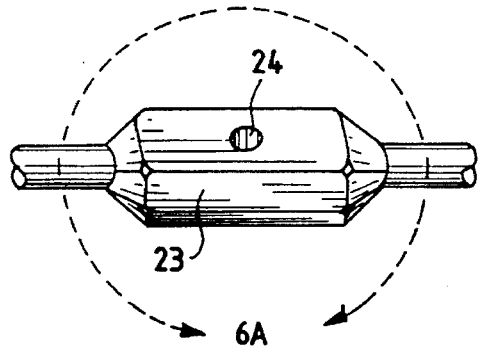
FIG. 5 is a perspective view of an alternative suction pressure diverter flow regulator valve.

Referring to FIG. 5 is a perspective view of an alternative suction pressure diverter flow regulator valve 6A consisting of an elastomer material 23 with a top wall orificial vent 24 opening inner cavity into ambient air at resting position.

Figure 6:
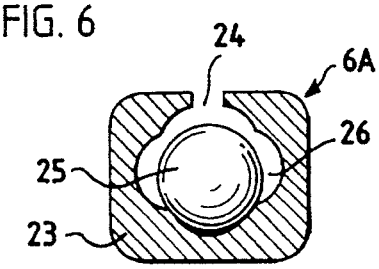
FIG. 6 is an schematic elevational mid-cross section view of alternative suction pressure diverter flow regulator valve at resting position.

Referring to FIG. 6 is an schematic elevational mid-cross section view of an alternate suction pressure diverter valve 6A at resting position consisting of an elastomer material 23 encasing a loosely fitted solid material 25. Top wall is provided with orificial vent 24 opening inner cavity or lumen 26 into ambient air.

Figure 7:
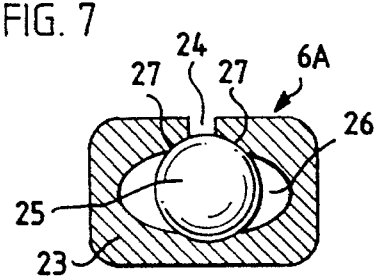
FIG. 7 is an schematic elevational mid-cross section view of an alternate suction pressure diverter flow regulator valve at external positive pressure end compression position.

Referring to FIG. 7 is an schematic elevational mid-cross section view of an alternate suction pressure diverter flow regulator valve 6A with external positive pressure applied at end-compression forming contact seal 27 of top wall inner surface of elastomer material 23 surrounding orificial vent 24 and surface of solid material 25 terminating inner cavity or lumen 26 communication to ambient air.

Figure 8:
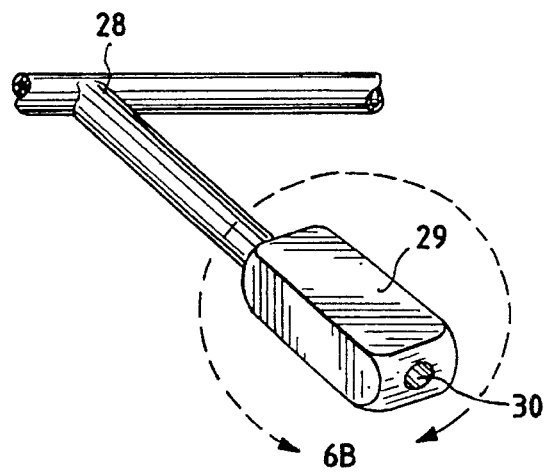
FIG. 8 is a perspective view of a second alternate suction pressure diverter flow regulator valve using Y-tubing and vented elastomer material.

Referring to FIG. 8 is a perspective view of a second alternative suction pressure diverter flow regulator valve 6B using Y-tubing 28 and elastomer material 29 with a terminal vent 30.

Figure 9:
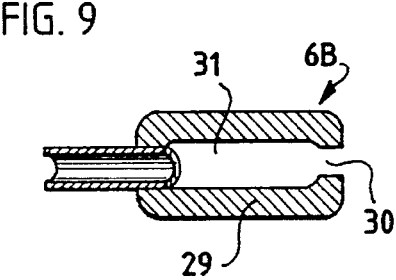
FIG. 9 is an schematic elevational mid-longitudinal cut section view of second alternative suction pressure diverter flow regulator valve using Y-tubing and vented elastomer material at resting position.

Referring to FIG. 9 is an schematic elevational mid-longitudinal cut section view of second alternative suction pressure diverter valve 6B using Y-tubing and elastomer material 29 with a terminal vent 30 open to ambient air at resting position.

Figure 10:
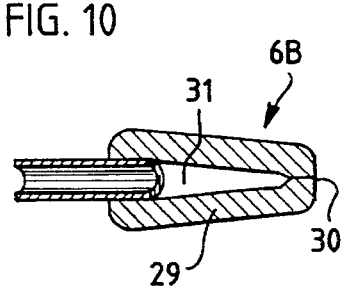
FIG. 10 is an schematic elevational mid-longitudinal cut section view of second alternative suction pressure diverter flow regulator valve using Y-tubing and vented elastomer material shown at end compression, i.e. external positive pressure applied.

Referring to FIG. 10 is an schematic elevational mid-longitudinal cut suction view of sections alternative suction pressure diverter flow regulator valve 6B using Y-tubing and elastomer material 29 with a terminal vent 30 sealed and closed to ambient air at end-compression position.

Figure 11:
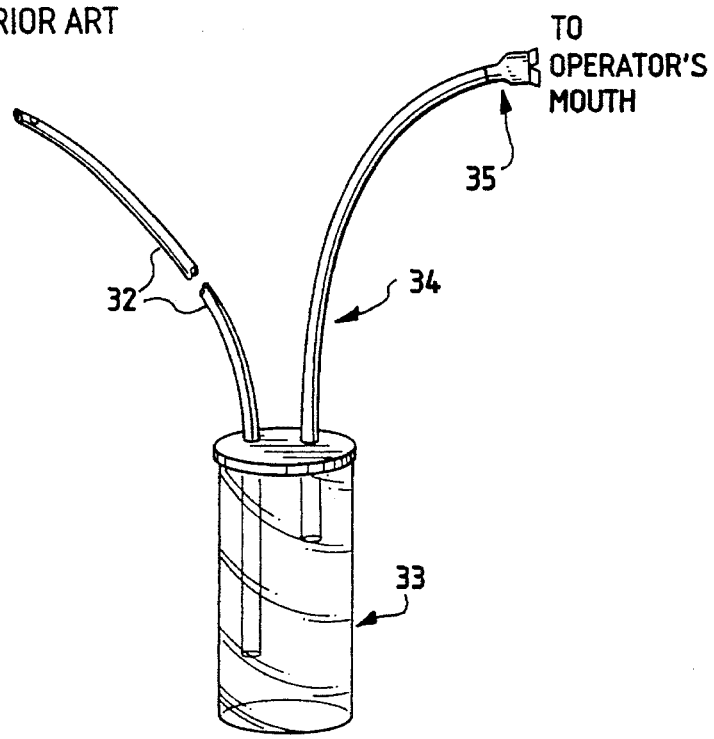
FIG. 11 is an schematic illustration of a device of prior art.

Referring to FIG. 11 is an schematic illustration of a device of prior art employing operator's mouth as source of suction consisting of catheter 32, mucus trap 33, mouthpiece tubing 34 and mouthpiece 35 connected in series in the order as above mentioned.

Figure 12:
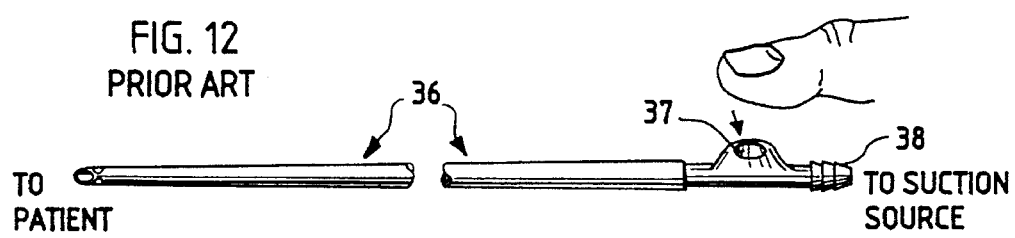
FIG. 12 is an schematic illustration of another device of prior art.
Figure 13:
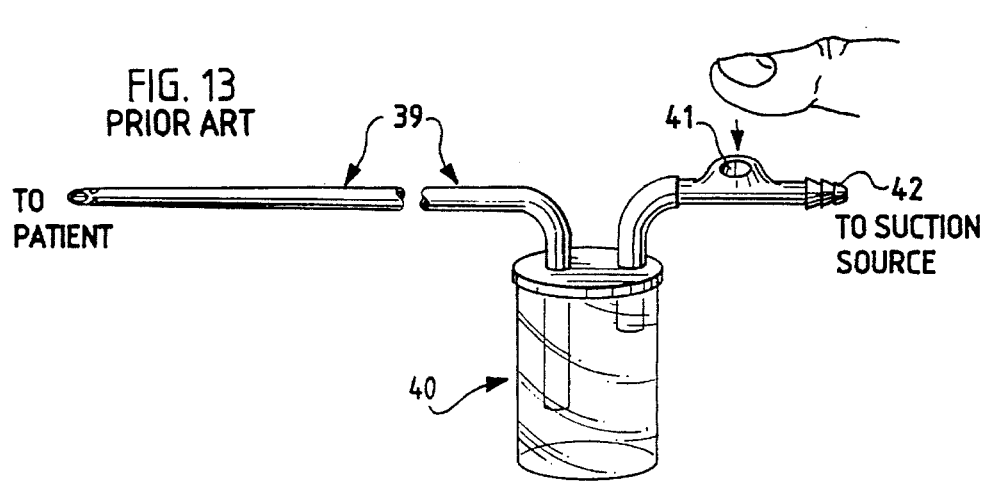
FIG. 13 is an schematic illustration of another device of prior art.

Referring to FIG. 12 is an schematic illustration of another device of prior art consisting of catheter 36, suction control vent 37 and suction tubing adapter 38 connected in series in the order as above mentioned. Similar to in principle of operation is another device of prior art as shown in schematic illustration in FIG. 13 consisting of catheter 39, mucus trap 40, suction control vent 41 and suction tubing adapter. Foregoing discussion described the principles of the prior art and its disadvantages offset by this present invention.

As various changes could be made in the construction of this present invention without departing from the scope of the invention, it is intended that all matter contained in the preceding discussions and drawings shall be interpreted as illustrative and not in a limiting sense.

I claim:

1. A body fluid suction device comprising means for collecting secretions from the nasopharynx;

means for transporting said secretions;

means for collecting and trapping said secretions;

means for generating a flow of said secretions; and means for regulating the flow of said secretions, said regulating means including an elastomer material having a cavity, said cavity having an opening to ambient air, and a solid material disposed within said cavity in proximity to said opening, whereby said means for regulating is actuated by pressing the elastomer material against said solid material.

\* \* \* \* \*